United States Patent [19]
Decoster

[11] Patent Number: 6,153,570
[45] Date of Patent: Nov. 28, 2000

[54] DETERGENT COSMETIC COMPOSITIONS AND USE

[75] Inventor: Sandrine Decoster, Epinay sur Seine, France

[73] Assignee: L'Oréal S.A., Paris, France

[21] Appl. No.: 09/194,971

[22] PCT Filed: Jun. 6, 1997

[86] PCT No.: PCT/FR97/01008

§ 371 Date: Apr. 19, 1999

§ 102(e) Date: Apr. 19, 1999

[87] PCT Pub. No.: WO97/46211

PCT Pub. Date: Dec. 11, 1997

[30] Foreign Application Priority Data

Jun. 7, 1996 [FR] France ................... 96 07193

[51] Int. Cl.⁷ ................ C11D 3/37; C11D 3/22; C11D 3/04
[52] U.S. Cl. .......... 510/122; 510/119; 510/121; 510/470; 510/471; 510/473; 510/466; 510/475; 510/476; 510/70.12; 510/70.122; 510/70.13
[58] Field of Search ............... 510/119, 121, 510/122, 470, 471, 473, 466, 475, 476; 424/70.12, 70.122, 70.13

[56] References Cited

U.S. PATENT DOCUMENTS

| | | | |
|---|---|---|---|
| 2,261,002 | 10/1941 | Ritter | 260/510 |
| 2,271,378 | 1/1942 | Searle | 167/22 |
| 2,273,780 | 2/1942 | Dittmar | 260/28 |
| 2,375,853 | 5/1945 | Kirby et al. | 260/583 |
| 2,388,614 | 11/1945 | Kirby et al. | 260/583 |
| 2,454,547 | 11/1948 | Bock et al. | 260/567.6 |
| 2,528,378 | 10/1950 | Mannheimer | 260/309.6 |
| 2,781,354 | 2/1957 | Mannheimer | 260/309.6 |
| 2,961,347 | 11/1960 | Floyd | 117/141 |
| 3,206,462 | 9/1965 | McCarty | 260/256.4 |
| 3,227,615 | 1/1966 | Korden | 162/87.1 |
| 3,589,578 | 6/1971 | Kamphausen | 226/40 |
| 3,874,870 | 4/1975 | Green et al. | 71/67 |
| 3,929,990 | 12/1975 | Green et al. | 424/78 |
| 3,966,904 | 6/1976 | Green et al. | 424/78 |
| 4,001,432 | 1/1977 | Green et al. | 424/329 |
| 4,005,193 | 1/1977 | Green et al. | 424/168 |
| 4,025,617 | 5/1977 | Green et al. | 424/78 |
| 4,025,627 | 5/1977 | Green et al. | 424/248.4 |
| 4,025,653 | 5/1977 | Green et al. | 424/325 |
| 4,026,945 | 5/1977 | Green et al. | 260/567.6 |
| 4,027,020 | 5/1977 | Green et al. | 424/248.56 |
| 4,031,307 | 6/1977 | DeMartino et al. | 536/114 |
| 4,915,938 | 4/1990 | Zawadzki et al. | 424/70 |
| 5,077,040 | 12/1991 | Bergmann et al. | 424/70 |
| 5,476,649 | 12/1995 | Naito et al. | 424/70.1 |
| 5,578,298 | 11/1996 | Berthiaume et al. | 424/70.122 |
| 5,783,535 | 7/1998 | Isobe et al. | 510/126 |

FOREIGN PATENT DOCUMENTS

| | | |
|---|---|---|
| 0 122 324 | 10/1984 | European Pat. Off. |
| 0 337 354 | 10/1989 | European Pat. Off. |
| 1 492 597 | 8/1967 | France |
| 1 583 363 | 10/1969 | France |
| 2 077 143 | 10/1971 | France |
| 2 080 759 | 11/1971 | France |
| 2 162 025 | 7/1973 | France |
| 2 190 406 | 2/1974 | France |
| 2 252 840 | 6/1975 | France |
| 2 270 846 | 12/1975 | France |
| 2 280 361 | 2/1976 | France |
| 2 316 271 | 1/1977 | France |
| 2 320 330 | 3/1977 | France |
| 2 336 434 | 7/1977 | France |
| 2 368 508 | 5/1978 | France |
| 2 393 573 | 1/1979 | France |
| 2 413 907 | 8/1979 | France |
| 2 470 596 | 6/1981 | France |
| 2 505 348 | 11/1982 | France |
| 2 519 863 | 7/1983 | France |
| 2 542 997 | 9/1984 | France |
| 2 598 611 | 11/1987 | France |

OTHER PUBLICATIONS

Chemical Abstracts, vol. 111, No. 12, Sep. 18, 1989 (JP 63 307 811).

M.R. Porter, "Handbook of Surfactants", Blackie & Son (Glasgow London), 1991, pp. 116–178.

English Language Derwent Abstract of FR 1 583 363.
English Language Derwent Abstract of FR 2 077 143.
English Language Derwent Abstract of FR 2 080 759.
English Language Derwent Abstract of FR 2 162 025.
English Language Derwent Abstract of FR 2 190 406.
English Language Derwent Abstract of FR 2 252 840.
English Language Derwent Abstract of FR 2 270 846.

(List continued on next page.)

Primary Examiner—Kery Fries
Attorney, Agent, or Firm—Finnegan, Henderson, Farabow, Garrett & Dunner, L.L.P.

[57] ABSTRACT

The invention discloses novel conditioning and detergent compositions comprising, in a cosmetically acceptable medium, (A) a washing base and (B) a conditioning system comprising at least one cationic polymer and an amine silicone of formula (I), in which: $R_1$, $R_2$, $R_3$ and $R_4$, identical or different, represent a $C_1$–$C_4$ alkyl radical or a phenyl grouping: $R_5$ represents a $C_1$–$C_4$ alkyl radical or a hydroxyl grouping: n is an integer from 1 to 5: m is an integer from 1 to 5: x is chosen such that the amine index is in a range between 0.01 and 1 meq/g. This invention is useful for hair washing and care.

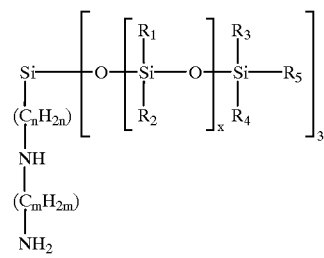

(I)

25 Claims, No Drawings

OTHER PUBLICATIONS

English Language Derwent Abstract of FR 2 280 361.
English Language Derwent Abstract of FR 2 316 271.
English Language Derwent Abstract of FR 2 320 330.
English Language Derwent Abstract of FR 2 336 434.
English Language Derwent Abstract of FR 2 368 508.
English Language Derwent Abstract of FR 2 393 573.
English Language Derwent Abstract of FR 2 413 907.
English Language Derwent Abstract of FR 2 470 596.
English Language Derwent Abstract of FR 2 505 348.
English Language Derwent Abstract of FR 2 519 863.
English Language Derwent Abstract of FR 2 542 997.
English Language Derwent Abstract of FR 2 598 611.

DETERGENT COSMETIC COMPOSITIONS AND USE

The present invention relates to novel cosmetic compositions with improved properties intended simultaneously for cleaning and conditioning the hair and comprising, in a cosmetically acceptable vehicle, a washing base composed of surfactants with a detergent power, in which base are also present, as conditioning agents, cationic polymers in combination with a specific silicone. The invention also relates to the use of the said compositions in the abovementioned cosmetic application.

The use of detergent compositions (or shampoos) based essentially on conventional surface-active agents of, in particular, anionic, non-ionic and/or amphoteric type but more particularly of anionic type is commonplace in the cleaning and/or washing of hair. These compositions are applied to wet hair and the foam generated by massaging or rubbing with the hands makes it possible, after rinsing with water, to remove the varied dirt initially present in the hair.

These base compositions certainly possess a good washing power but the intrinsic cosmetic properties which are attached thereto however remain fairly weak in particular due to the fact that the relatively aggressive nature of such a cleaning treatment can in the long term cause more or less marked damage to the capillary fibre, related in particular to the gradual removal of the lipids or proteins contained in or at the surface of the latter.

Thus, in order to improve the cosmetic properties of the above detergent compositions and more particularly of those which are required to be applied to sensitive hair (i.e. hair which is damaged or embrittled, in particular under the chemical action of atmospheric agents and/or of hair treatments, such as permanent waves, dyeings or bleachings), it is now usual to introduce, into the latter, additional cosmetic agents, known as conditioning agents, intended mainly to repair or restrict the harmful or undesirable effects induced by the various treatments or attacks which capillary fibres are more or less repeatedly subjected to. These conditioning agents can, of course, also improve the cosmetic behaviour of natural hair.

The conditioning agents which are most commonly used currently in shampoos are cationic polymers, silicones and/or silicone derivatives, because these conner, on washed, dry or wet hair, an ease of disentangling, a softness and a sleekness which are increased with respect to that which can be obtained with the corresponding cleaning compositions which are devoid of them. In addition, it is known to preferably use a mixture of silicone and of cationic polymer on sensitive hair.

However, and despite the progress recently made in the field of shampoos based on cationic polymers and on silicone, these are not really completely satisfactory, so that a great need still currently exists with respect to being able to have available novel products exhibiting better performances with respect to one or more of the cosmetic properties listed above.

The present invention is targeted at satisfying such a need.

Thus, following significant research carried out on the subject, it has now been found by the Applicant Company, entirely unexpectedly and surprisingly, that by using a specific and suitably selected amine-containing silicone as defined below in detergent compositions containing conventional cationic polymers as conditioning agents, it is possible to substantially and significantly improve the cosmetic properties attached to these compositions while retaining their good intrinsic washing power.

The compositions in accordance with the invention confer on hair, after rinsing, a notable treating effect which is expressed in particular by an ease of disentangling as well as a contribution of body, of lightness, of sleekness, of softness and of suppleness.

All these discoveries form the basis of the present invention.

Thus, according to the present invention, novel detergent and conditioning compositions are now provided comprising, in a cosmetically acceptable medium, (A) a washing base and (B) a conditioning system comprising at least one cationic polymer and at least one specific amine-containing silicone of formula (I):

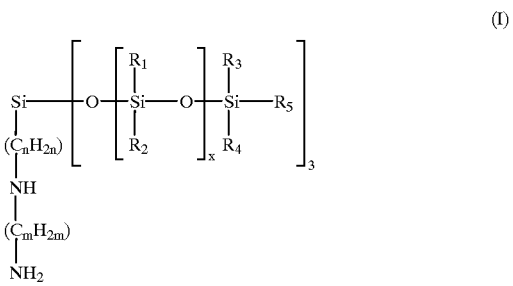

in which:

R$_1$, R$_2$, R$_3$ and R$_4$, which are identical or different, denote a C$_1$–C$_4$ alkyl radical or a phenyl group, R$_5$ denotes a C$_1$–C$_4$ alkyl radical or a hydroxyl group, n is an integer varying from 1 to 5, m is an integer varying from 1 to 5, and in which x is chosen so that the amine number is between 0.01 and 1 meq/g.

Another subject-matter of the invention is the use in cosmetics of the above compositions for cleaning and conditioning the hair.

However, other characteristics, aspects and advantages of the invention will become still more clearly apparent on reading the description which follows and the concrete but in no way limiting examples intended to illustrate it.

As indicated above, the essential components entering into the composition of the products according to the invention are (A) a washing base and (B) a conditioning system comprising (i) the cationic polymer or polymers and (ii) the specific amine-containing silicone or silicones.

A—WASHING BASE

The compositions in accordance with the invention necessarily comprise a washing base, generally an aqueous washing base.

The surfactant or surfactants forming the washing base can be chosen without distinction, alone or as mixtures, from anionic, amphoteric, non-ionic, zwitterionic and cationic surfactants.

However, according to the invention, the washing base preferably comprises anionic surfactants or mixtures of anionic surfactants and of amphoteric surfactants and, more preferentially still, contains only this type of surfactant or mixture of surfactants.

The minimum amount of washing base is that just sufficient to confer a satisfactory foaming and/or detergent power on the final composition, and excessively large amounts of washing base do not really contribute additional advantages.

Thus, according to the invention, the washing base can represent from 4% to 50% by weight, preferably from 10% to 35% by weight and more preferentially still from 12% to 25% by weight of the total weight of the final composition.

The surfactants which are suitable for implementing the present invention are in particular the following:

(i) Anionic surfactant(s)

Their nature does not assume a really critical character within the context of the present invention.

Thus, by way of example of anionic surlactants that can be used, alone or as mixtures, in the context of the present invention, there may be mentioned in particular (non-limiting list) the salts (in particular alkali metal, especially sodium, salts, ammonium salts, amine salts, aminoalcohol salts or magnesium salts) of the following compounds: alkyl sulphates, alkyl ether sulphates, alkylamido ether sulphates, alkylarylpolyether sulphates, monoglyceride sulphates; alkylsulphonates, alkyl phosphates, alkylamidesuldhonates, alkylarylsulphonates, α-olefinsulphonates, paraffinsulphonates; alkyl sulphosuccinates, alkyl ether sulphosuccinates, alkylamidesulphosuccinates; alkyl sulphosuccinamates; alkyl sulphoacetates; alkyl ether phosphates; acylsarcosinates; acylisethionates and N-acyltaurates, the alkyl or acyl radical of all these different compounds preferably comprising from 12 to 20 carbon atoms, and the aryl radical preferably denoting a phenyl or benzyl group. Among the anionic surfactants which are further usable, there may also be mentioned the salts of fatty acids such as the salts of oleic, ricinoleic, palmitic and stearic acids, the acids of copra oil or of hydrogenated copra oil, and acyllactylates in which the acyl radical comprises 8 to 20 carbon atoms. It is also possible to use weakly anionic surfactants, like alkyl-D-galactosideuronic acids and salts thereof, as well as polyoxyalkylenated ether carboxylic acids and salts thereof, in particular those comprising from 2 to 50 ethylene oxide groups, and mixtures thereof. The anionic surfactants of the polyoxyalkylenated ether carboxylic acid or salt type are in particular those which correspond to the following formula (1):

$$R_1-(OC_2H_4)_n-OCH_2COOA \quad (1)$$

in which:

$R_1$ denotes an alkyl or alkaryl group and n is an integer or decimal number (mean value) which can vary from 2 to 24 and preferably from 3 to 10, the alkyl radical having between 6 and 20 carbon atoms approximately and aryl preferably denoting phenyl, A denotes H, ammonium, Na, K, Li, Mg or a monoethanolamine or triethanolamine residue. Use may also be made of mixtures of compounds of formula (1), in particular mixtures in which the $R_1$ groups are different.

Among the anionic surfactants, it is preferable to use, according to the invention, alkyl sulphate and alkyl ether sulphate salts and mixtures thereof.

(ii) Non-ionic surfactant(s)

The non-ionic surface-active agents themselves are also compounds which are well known per se (in this respect see in particular the "Handbook of Surfactants" by M. R. Porter, published by Blackie & Son (Glasgow and London), 1991, pp. 116–178) and, in the context of the present invention, their nature does not assume any critical character. They can thus be chosen especially from (non-limiting list) alcohols, alpha-diols, alkylphenols or polyethoxylated, polypropoxylated or polyglyccrolated fatty acids which have a fatty chain comprising, for example, 8 to 18 carbon atoms, it being possible for the number of ethylene oxide or propylene oxide groups to range especially from 2 to 50 and it being possible for the number of glycerol groups to range especially from 2 to 30. The copolymers of ethylene and propylene oxide and the condensates of ethylene and propylene oxide with fatty alcohols may also be mentioned; the polyethoxylated fatty amides preferably having from 2 to 30 mol of ethylene oxide, the polyglycerolated fatty amides on average containing 1 to 5 glycerol groups and in particular 1.5 to 4; the polyethoxylated fatty amines prererably having 2 to 30 mol of ethylene oxide; the oxyethylenated esters of sorbitan fatty acids having from 2 to 30 mol of ethylene oxide; the sucrose esters of fatty acids, the polyethylene glycol esters of fatty acids, alkylpolyglycosides, the N-alkylglucamine derivatives, amine oxides such as the oxides of $(C_{10}-C_{14})$alkylamines or the N-acylaminopropylmorpholine oxides. It will be noted that alkylpolyglycosides constitute non-ionic surfactants which enter particularly well into the scope of the present invention.

(iii Amphoteric or zwitterionic surfactant(s)

The amphoteric or zwitterionic surface-active agents, the nature of which does not assume any critical character in the context of the present invention, may be especially (non-limiting list) derivatives of aliphatic secondary or tertiary amines in which the aliphatic radical is a linear or branched chain comprising 8 to 18 carbon atoms and containing at least one water-solubilizing anionic group (for example carboxylate, sulphonate, sulphate, phosphate or phosphonate); $(C_8-C_{20})$alkylbetaines, sulphobetaines, $(C_8-C_{20})$alkylamido$(C_1-C_6)$alkylbetaines or $(C_8-C_{20})$alkylamido$(C_1-C_6)$alkylsulphobetaines may further be mentioned.

Among the amine derivatives, there may be mentioned products sold under the name Miranol, as described in U.S. Pat. Nos. 2,528,378 and U.S. Pat. No. 2,731,354 and classified in the CTFA dictionary, 3rd edition, 1982, under the names Amphocarboxyglycinates and Amphocarboxypropionates with respective structures:

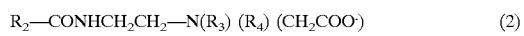

$$R_2-CONHCH_2CH_2-N(R_3)(R_4)(CH_2COO^-) \quad (2)$$

in which:

$R_2$ denotes an alkyl radical of an acid $R_2$—COOH present in hydrolysed copra oil, a heptyl, nonyl or undecyl radical, $R_3$ denotes a beta-hydroxyethyl group and $R_4$ a carboxymethyl group; and

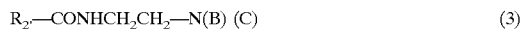

$$R_2-CONHCH_2CH_2-N(B)(C) \quad (3)$$

in which:

B represents —$CH_2CH_2OX'$, C represents —$(CH_2)_z$—Y', with z=1 or 2,

X' denotes the —$CH_2CH_2$—COOH group or a hydrogen atom

Y' denotes —COOH or the radical —$CH_2$—CHOH—$SO_3H$ $R_2$, denotes an alkyl radical of an acid $R_9$—COOH present in copra oil or in hydrolysed linseed oil, an alkyl radical, in particular $C_7$, $C_9$, $C_{11}$ or $C_{13}$, a $C_{17}$ alkyl radical and its iso form or an unsaturated radical $C_{17}$.

By way of example, there may be mentioned the coco-amphocarboxyglycinate sold under the trade name Miranol C2M concentrated by the Company Miranol.

(iv) Cationic surfactants

Among the cationic surfactants, there may be mentioned in particular (non-limiting list): the salts of optionally polyoxyalkylenated primary, secondary or tertiary fatty amines; quaternary ammonium salts, such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature. It will be noted that the cationic surfactants, the use of which is not ruled out, do not constitute preferred surfactants for making use of the present invention.

B—CONDITIONING SYSTEM (i) Cationic polymer(s)

The compositions according to the invention, in addition, necessarily comprise a cationic polymer.

The conditioning agents of cationic polymer type which can be used in accordance with the present invention can be chosen from all those already known per se as improving the cosmetic properties of hair treated with detergent compositions, namely, in particular, those disclosed in Patent Application EP-A 0,337,354 and in French Patent Applications FR-A-2,270,846, 2,383,660, 2,598,611, 2,470, 596 and 2,519,863.

More generally still, within the meaning of the present invention, the expression "cationic polymer" denotes any polymer containing cationic groups and/or groups which can be ionized to cationic groups.

The preferred cationic polymers are chosen from those which comprise units containing primary, secondary, tertiary and/or quaternary amine groups, which can either form part of the main polymer chain or be carried by a side substituent directly connected to the latter.

The cationic polymers used generally have a number-average molecular mass of between 500 and $5 \times 10^6$ approximately and preferably of between $10^3$ and $3 \times 10^6$ approximately.

Mention may more particularly be made, among cationic polymers, of quaternized proteins (or protein hydrolysates), and polymers of the polyamine, polyaminoamide and poly (quaternary ammonium) type. These are known products.

The quaternized proteins or protein hydrolysates are in particular chemically modified polypeptides carrying quaternary ammonium groups at the chain end or grafted onto the chain. Their molecular mass can vary, for example, from 1500 to 10,000 and in particular from 2000 to 5000 approximately. Mention may in particular be made, among these compounds, of:

collagen hydrolysates carrying triethylammonium groups, such as the products sold under the name "Quat-Pro E" by the Company Maybrook and called, in the CTFA dictionary, "Triethonium Hydrolyzed Collagen Ethosulphate";

collagen hydrolysates carrying trimethylammonium and trimethylstearylammonium chloride groups, sold under the name of "Quat-Pro S" by the Company Maybrook and called, in the CTFA dictionary, "Steartrimonium Hydrolyzed Collagen";

animal protein hydrolysates carrying trimethylbenzylammonium groups, such as the products sold under the name "Crotein BTA" by the Company Croda and called, in the CTFA dictionary, "Benzyltrimonium Hydrolysed Animal Protein";

protein hydrolysates carrying, on a polypeptide chain, quaternary ammonium groups comprising at least one alkyl radical having from 1 to 18 carbon atoms.

Mention may be made, among these protein hydrolysates, inter alia, of:

"Croquat L", the quaternary ammonium groups of which comprise a $C_{12}$ alkyl group;

"Croquat M", the quaternary ammonium groups of which comprise $C_{10}$–$C_{18}$ alkyl groups;

"Croquat S", the quaternary ammonium groups of which comprise a $C_{18}$ alkyl group;

"Crotein Q", the quaternary ammonium groups of which comprise at least one alkyl group having from 1 to 18 carbon atoms.

These various products are sold by the Company Croda.

Other quaternized proteins or hydrolysates are, for example, those corresponding to the formula:

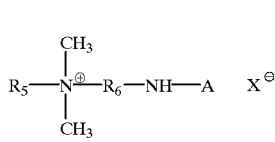

(II)

in which $X^-$ is an anion of an organic or inorganic acid, A denotes a protein residue derived from collagen protein hydrolysates, $R_5$ denotes a lipophilic group comprising up to 30 carbon atoms and $R_6$ represents an alkylene group having 1 to 6 carbon atoms. Mention may be made, for example, of the products sold by the Company Inolex under the name "Lexein QX 3000", called "Cocotrimonium Collagen Hydrolysate" in the CTFA dictionary.

Mention may also be made of quaternized plant proteins, such as wheat, maize or soya proteins: mention may be made, as quaternized wheat proteins, of those sold by the Company Croda under the names "Hydrotriticum WQ or QM", called "Cocodimonium Hydrolysed Wheat Protein" in the CTFA dictionary, "Hydrotriticum QL", called "Laurdimonium Hydrolysed Wheat Protein" in the CTFA dictionary or "Hydrotriticum QS", called "Steardimonium Hydrolysed Wheat Protein" in the CTFA dictionary.

The polymers of the polyamine, polyaminoamide or poly (quaternary ammonium) type which can be used in accordance with the present invention which can be mentioned in particular are those disclosed in French Patents No. 2,505, 348 or 2,542,997. Mention may be made, among these polymers, of:

(1) optionally quaternized vinylpyrrolidone/dialkylaminoalkyl acrylate or methacrylate copolymers, such as the products sold under the name "Gafquat" by the Company ISP, such as, for example, Gafquat 734, 755 or HS100, or else the product "Copolymer 937". These polymers are disclosed in detail in French Patents 2,077,143 and 2,393,573.

(2) cellulose ether derivatives comprising quaternary ammonium groups disclosed in French Patent 1,492, 597 and in particular the polymers sold under the names "JR" (JR 400, JR 125, JR 30M) or "LR" (LR 400, LR 30M) by the Company Union Carbide Corporation. These polymers are also defined in the CTFA dictionary as quaternary ammoniums of hydroxyethylcellulose which has reacted with an epoxide substituted by a trimethyl-ammonium group.

(3) cationic cellulose derivatives, such as the copolymers of cellulose or the cellulose derivatives grafted with a water-soluble quaternary ammonium monomer and disclosed in particular in U.S. Pat. No. 4,131,576, such as hydroxyalkyl celluloses, for example hydroxymethyl, hydroxyethyl or hydroxypropyl celluloses, grafted in particular with a methacryloylethyltrimethylammonium, methacrylamido-propyltrimethylammonium or diallyldimethylammonium salt.

The marketed products corresponding to this definition are more particularly the products sold under the name "Celquat L 200" and "Celquat H 100" by the Company National Starch.

(4) the cationic polysaccharides disclosed more particularly in U.S. Pat. Nos. 3,589,578 and 4,031,307, such as guar gums containing cationic trialkylammonium groups. Use is made, for example, of guar gum modified by a 2,3-epoxypropyltrimethylammonium salt (for example, chloride).

Such products are sold in particular under the trade names of Jaguar C13 S, Jaguar C 15, Jaguar C 17 or Jaguar C162 by the Company Meyhall.

(5) polymers composed of piperazinyl units and of divalent, straight- or branched-chain alkylene or hydroxyalkylene radicals, optionally interrupted by oxygen, sulphur or nitrogen atoms or by aromatic or heterocyclic rings, as well as the oxidation and/or quaternization products of these polymers. Such polymers are disclosed in particular in French Patents 2,162,025 and 2,280,361.

(6) water-soluble polvaminoamides prepared in particular by polycondensation of an acidic compound with a polyamine; these polyaminoamides can be crosslinked by an epihalohydrin, a diepoxide, a dianhydride, an unsaturated dianhydride, a bisunsaturated derivative, a bishalohydrin, a bisazetidinium, a bishaloacyldiamine or an alkyl bishalide or alternatively by an oligomer resulting from the reaction of a bifunctional compound reactive with respect to a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mol per amine group of the polyaminoamide; these polyaminoamides can be alkylated or, if they comprise one or more tertiary amine functional groups, quaternized. Such polymers are disclosed in particular in French Patents 2,252,840 and 2,368,508.

(7) polyaminoamide derivatives resulting from the condensation of polyalkylenepolyamines with polycarboxylic acids, followed by an alkylation by bifunctional agents. Mention may be made, for example, of adipic acid/dialkylaminohydroxyalkyl/dialkylenetriamine polymers in which the alkyl radical comprises from 1 to 4 carbon atoms and preferably denotes methyl, ethyl or propyl. Such polymers are disclosed in particular in French Patent 1,583,363.

Mention may more particularly be made, among these derivatives, of the adipic acid/dimethylaminohydroxypropyl/diethylenetriamine polymers sold under the name "Cartaretine F, F4 or F8" by the Company Sandoz.

(8) polymers obtained by reaction of a polyalkylenepolyamine comprising two primary amine groups and at least one secondary amine grouo with a dicarboxylic acid chosen from diglycolic acid and saturated aliphatic dicarboxylic acids having from 3 to 8 carbon atoms. The molar ratio of polyalkylenepolyamine to dicarboxylic acid being between 0.8:1 and 1.4:1; the polyaminoamide resulting therefrom being brought to react with epichlorohydrin in a molar ratio of epichlorohydrin in relation to the secondary amine group of the polyaminoamide of between 0.5:1 and 1.8:1. Such polymers are disclosed in particular in U.S. Pat. Nos. 3,227,615 and 2,961,347.

Polymers of this type are in particular sold under the name "Hercosett 57" by the Company Hercules Inc. or else under the name of "PD 170" or "Delsette 101" by the Company Hercules in the case of the adipic acid/epoxypropyl/diethylenetriamine copolymer.

(9) cyclohomopolymers of methyldiallylamine or of dimethyldiallylammonium, such as the homopolymers comprising, as main constituent of the chain, units corresponding to the formulae (VI) or (VI'):

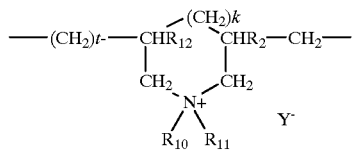

(VI)

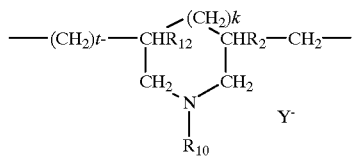

(VI')

in which formulae k and t are equal to 0 or 1, the sum k+t being equal to 1; $R_{12}$ denotes a hydrogen atom or a methyl radical; $R_{10}$ and $R_{11}$, independently of one another, denote an alkyl group having from 1 to 22 carbon atoms, a hydroxyalkyl group in which the alkyl group preferably has 1 to 5 carbon atoms or a lower amidoalkyl group or $R_{10}$ and $R_{11}$ can denote, jointly with the nitrogen atom to which they are attached, heterocyclic groups, such as piperidinyl or morpholinyl; $Y^-$ is an anion, such as bromide, chloride, acetate, borate, citrate, tartrate, bisulphate, bisulphite, sulphate or phosphate. These polymers are disclosed in particular in French Patent 2,080,759 and in its Certificate of Addition 2,190,406.

Mention may more particularly be made, among the polymers defined above, of the homopolymer of diallydiffiethylammonium chloride sold under the name "Merquat 100" by the Company Merck.

(10) the quaternary diammonium polymer comprising repeat units corresponding to the formula:

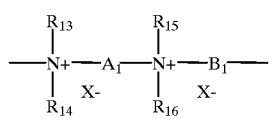

(VII)

in which formula (VII):

$R_{13}$, $R_{14}$, $R_{15}$ and $R_{16}$, which are identical or different, represent aliphatic, alicyclic or arylaliphatic radicals comprising from 1 to 20 carbon atoms or lower hydroxyalkyl aliphatic radicals or else $R_{13}$, $R_{14}$, $R_{15}$ and $R_{16}$, together or separately, form, with the nitrogen atoms to which they are attached, heterocycles optionally comprising a second heteroatom other than nitrogen or else $R_{13}$, $R_{14}$, $R_{15}$ and $R_{16}$ represent a linear or branched $C_1$–$C_6$ alkyl radical substituted by a nitrile, ester, acyl, amide or —CO—O—$R_{17}$—D or —CO—NH—$R_{17}$—D group, where $R_{17}$ is an alkylene and D a quaternary ammonium group;

$A_1$ and $B_1$ represent polymethylene groups comprising from 2 to 20 carbon atoms which can be linear or branched, saturated or unsaturated, and which can contain, bonded to or inserted into the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a $(CH_2)_n$—CO—D—OC—$(CH_2)_n$-group in which D denotes:

a) a glycol residue of formula: —O—Z—O—, where Z denotes a linear or branched hydrocarbon-comprising radical or a group corresponding to one of the following formulae:

—(CH$_3$—CH$_3$—O)$_x$—CH$_2$—CH$_2$—

—[CH$_2$—CH (CH$_3$)—O]$_y$—CH$_2$—CH(CH$_3$)— where x and y denote an integer from 1 to 4, representing a defined and unique degree of polymerization, or any number from 1 to 4 representing a mean degree of polymerization;

b) a bis-secondary diamine residue, such as a piperazine derivative;

c) a bisprimary diamine residue of formula: —NH—Y—NH—, where Y denotes a linear or branched hydrocarbon-comprising radical or else the divalent radical

—CH$_2$—CH$_2$—S—S—CH$_2$—CH$_2$—;

d) a ureylene group of formula: —NH—CO—NH—;

Preferably, $X^-$ is an anion, such as chloride or bromide.

These polymers have a number-average molecular mass generally of between 1000 and 100,000.

Polymers of this type are disclosed in particular in French Patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) polymers of poly(quarernary ammonium)s composed of units of formula (VIII):

X denotes the halogen atom,

A denotes a radical from a dihalide or preferably represents —CH$_2$—CH$_2$—O—CH$_2$—CH$_2$—.

Such compounds are disclosed in particular in Patent Application EP-A-122,324.

Mention may be made among these, for example, of the products "Mirapol A 15", "Mirapol AD1", "Mirapol AZ1" and "Mirapol 175", sold by the company Miranol.

(12) homopolymers or copolymers derived from acrylic or methacrylic acids and comprising units:

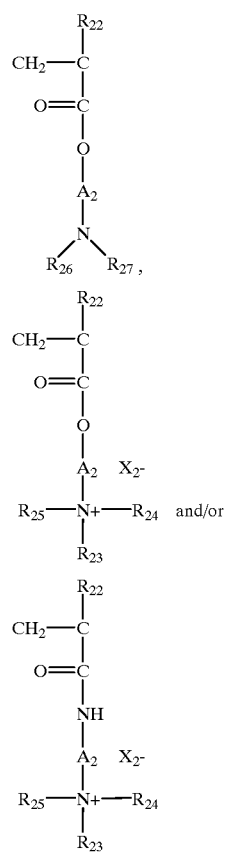

in which the $R_{22}$ groups independently denote H or CH$_3$, (VIII)

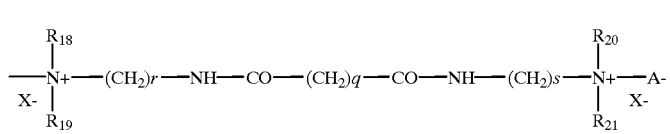

in which formula:

$R_{18}$, $R_{19}$, $R_{20}$ and $R_{21}$, which are identical or different, represent a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer or between 1 and 6, with the proviso that $R_{18}$, $R_{19}$, $R_{20}$ and $R_{21}$ do not simultaneously represent a hydrogen atom, r and s, which are identical or different, are integers of between 1 and 6, q is equal to 0 or to an integer of between 1 and 34, the $A_1$ groups independently denote a linear or branched alkyl group of 1 to 6 carbon atoms or a hydroxyalkyl group of 1 to 4 carbon atoms, the $R_{23}$, $R_{24}$ and $R_{25}$ groups, which are identical or different, independently denote an alkyl group of 1 to 18 carbon atoms or a benzyl radical, the $R_{26}$ and $R_{27}$ groups represent a hydrogen atom or an alkyl group of 1 to 6 carbon atoms, $X_2^-$ denotes an anion, for example methyl sulphate or halide, such as chloride or bromide.

The comonomer or comonomers which can be used in the preparation of the corresponding copolymers belong to the family of acrylamides, methacrylamides, diacetone acrylamides, acrylamides and methacrylamides substituted at the nitrogen by lower alkyls, alkyl esters of acrylic or methacrylic acids, vinyl-pyrrolidone or vinyl esters.

(13) quaternary polymers of vinylpyrrolidone and vinylimidizole, such as, for example, the products sold under the names Luviquat FC 905, FC 550 and FC 370 by the Company B.A.S.F.

(14) polyamines, such as Polyquart H sold by Henkel, referenced under the name "Polyethylene Glycol (15) Tallow Polyamine" in the CTFA dictionary.

(15) crosslinked polymers of methacryloyloxyethyltrimethylammonium chloride, such as the polymers obtained by homopolymerization of dimethylaminoethyl methacrylate quaternized by methyl chloride or by copolymerization of acrylamide with dimethylaminoethyl methacrylate quaternized by methyl chloride, the homo- or copolymerization being followed by a crosslinking by a compound possessing olefinic unsaturation, in particular methylenebisacrylamide. Use may more particularly be made of a crosslinked acrylamide/methacryloyloxyethyltrimethylammonium chloride (20/80 by weight) copolymer in the form of a dispersion containing 50% by weight of the said copolymer in mineral oil. This dispersion is sold under the name of "Salcare SC 92" by the Company Allied Colloids. Use may also be made of a crosslinked homopolymer of methacryloyloxyethyltrimethylammonium chloride containing approximately 50% by weight of the homopolymer in mineral oil. This dispersion is sold under the name of "Salcare SC 95" by the Company Allied Colloids.

Other cationic polymers which can be used in the context of the invention are polyalkyleneimines, in particular polyethyleneimines, polymers comprising vinylpyridine or vinylpyridinium units, condensates of polyamines and of epichlorohydrin, quaternary polyureylenes and chitin derivatives.

According to the invention, use may more particularly be made of polymers chosen from Mirapol, the compound of formula (VII) in which $R_{13}$, $R_{14}$, $R_{15}$ and $R_{16}$ represent the methyl radical, $A_1$ represents the radical of formula —$(CH_2)_3$— and $B_1$ represents the radical of formula —$(CH_2)_6$— and $X^-$ represents the chloride anion (subsequently called Mexomere PO) and the compound of formula (VII) in which $R_{13}$ and $R_{14}$ represent the ethyl radical, $R_{15}$ and $R_{16}$ represent the methyl radical, $A_1$ and $B_1$ represent the radical of formula —$(CH_2)_3$— and X represents the bromide anion (subsequently called Mexomere PAK).

Among all the cationic polymers capable of being used in the context of the present invention, it is preferable to employ quaternary cellulose ether derivatives, such as the products sold under the name "JR 400" by the Company Union Carbide Corporation, cyclopolymers, in particular the copolymers of dimethyldiallylammonium chloride and of acrylamide sold under the names "Merquat 550" and "Merquat S" by the Company Merck, or cationic polysaccharides and more particularly the guar gum modified by 2,3-epoxypropyltrimethylammonium chloride sold under the name "Jaguar C13S" by the Company Meyhall.

According to the invention, the cationic polymer or polymers can represent from 0.001% to 10% by weight, preferably from 0.005% to 5% by weight and more preferably still from 0.01% to 3% by weight of the total weight of the final composition.

(ii) Amine-containing silicones

According to an essential characteristic of the detergent compositions in accordance with the invention, the latter additionally contain at least one amine-containing silicone of formula (I) defined above.

Use is preferably made of the amine-containing silicones of general formula (I) which correspond to at least one of the, and preferably to all the, following conditions:

$R_1$, $R_2$, $R_3$ and $R_4$ denote the methyl radical, $R_5$ denotes the methyl radical, n is equal to 3, m is equal to 2.

The ($C_nH_{2n}$) and ($C_mH_{2m}$) groups can be linear or branched.

Such silicones are, for example, sold under the names SF1921 or SF1925 by the Company General Electric.

The cosmetic compositions in accordance with the invention contain the amine-containing silicones defined above at contents by weight which can be between 0.05% and 10%, preferably between 0.1% and 5% and more preferably still between 0.2% and 3% with respect to the total weight of the composition.

The vehicle, or carrier, of the detergent compositions according to the invention is preferably water or an aqueous/alcoholic solution of a lower alcohol, such as ethanol, isopropanol or butanol.

The detergent compositions according to the invention exhibit a final pH generally of between 3 and 10. This pH is preferably between 5 and 8. The adjustment of the pH to the desired value can be carried out conventionally by addition of a base (organic or inorganic) to the composition, for example aqueous ammonia or a primary, secondary or tertiary (poly)amine, such as monoethanolamine, diethanolamine, triethanolamine, isopropanolamine or 1,3-propane-diamine, or alternatively by addition of an acid, referably a carboxylic acid, such as, for example, citric acid.

The detergent compositions according to the invention can, of course, additionally contain all the usual adjuvants encountered in the field of shampoos, such as, for example, fragrances, preservatives, sequestering agents, thickeners, softeners, foam-modifying agents, colorants, pearlescent agents, moisturizing agents, antidandruff or antiseborrhoeic agents, vitamins, sunscreens, suspending agents and others.

Of course, a person skilled in the art will take care to choose this or these possible additional compounds and/or their amounts so that the advantageous properties intrinsically attached to the quaternary combination (washing base+cationic polymer+a specific silicone) in accordance with the invention are not, or not substantially, detrimentally affected by the envisaged addition or additions.

These compositions can be provided in the form of more or less thickened liquids, of creams or of gels and they are mainly suitable for washing, caring for and/or styling the hair. They can also be provided in the form of rinse-out lotions.

When the compositions in accordance with the invention are employed as conventional shampoos, they are simply applied to wet hair and the foam generated by massaging or rubbing with the hands is then removed, after an optional period of rest, by rinsing with water, it being possible for the operation to be repeated one or more times.

Another subject-matter of the invention is a process for washing and for conditioning keratinous fibres, such as the hair, which consists in applying, to the said wetted fibres, an effective amount of a composition as defined above and in then rinsing with water, after an optional period of rest.

As indicated above, the compositions in accordance with the invention confer on the hair, after rinsing, a notable styling effect which is expressed in particular by an ease of styling and of form retention, as well as a contribution of body and of lightness, which are markedly improved.

A concrete but in no way limiting example illustrating the invention will now be given.

EXAMPLE

Two shampoo compositions were prepared, one in accordance with the invention (composition A) and the other comparative (composition B):

|  | A Invention | B Comparative |
|---|---|---|
| Sodium lauryl ether sulphate (70/30 $C_{12}/C_{14}$) containing 2.2 mol of ethylene oxide as an aqueous solution containing 28% of AM (AM = active material) | 14 g AM | 14 g AM |
| Miranol C2M(*) | 4.6 g AM | 4.6 g AM |
| Ammonium lauryl sulphate as an aqueous solution containing 30% of AM | 1 g | 1 g |
| Cationic polymer (**) | 0.1 g | 0.1 g |
| Amine-containing silicone according to the invention (***) | 2.5 g AM | — |
| Amine-containing silicone (****) | — | 2.5 g |
| Stearyl alcohol | 1.59 g | 1.59 g |
| Cetylstearyl alcohol (30/70) oxyethylenated with 33 mol of ethylene oxide | 0.3 g | 0.3 g |
| Cetyl alcohol | 1.11 g | 1.11 g |
| Monoisopropanolamide of copra acids | 2.5 g | 2.5 g |
| Citric acid, q.s. pH | 5 | 5 |
| Demineralized water, q.s. | 100 g | 100 g |

(*): Sodium cocoamidoethyl(N-hydroxyethyl-N-carboxymethyl)glycinate, sold by Rhône-Poulenc
(**): Guar gum modified by 2,3-epoxypropyltrimethylammonium chloride, sold under the name Jaguar C13 S by the company Rhône-Poulenc
(***): Amine-containing silicone of formula:

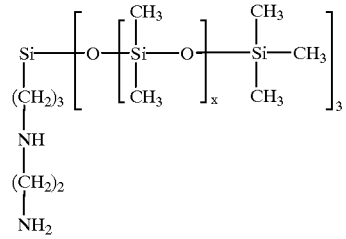

in which x is chosen so that the amine number is approximately 0.5 meq/g.
(SF1921 from General Electric).
(****): Amodimethicone, sold as a cationic emulsion containing 35% of active material under the name Fluid DC 939 by the company Dow Corning Shampooing is carried out by applying approximately 12 g of the composition A to sensitive hair which has been wetted beforehand. The shampoo is made to foam and then copious rinsing is carried out with water.

The same procedure is carried out as above with the comparative compositions B and C.

A panel of experts evaluates the disentangling of the wetted hair, the disentangling of the dried hair, and the ease of shaping, the softness and the sleekness of the dried hair.

All the experts indicate a marked improvement in these properties for the hair treated with the composition A according to the invention.

What is claimed is:

1. A detergent and conditioning composition, said composition comprising (A) a washing base, and (B) a conditioning system, wherein said conditioning system comprises at least one cationic polymer and at least one amine-containing silicone of formula (I):

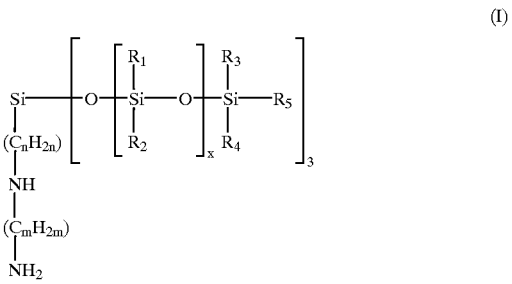

in which:
$R_1$, $R_2$, $R_3$ and $R_4$ are identical or different and denote a $C_1$–$C_4$ alkyl radical or a phenyl group,
$R_5$ denotes a $C_1$–$C_4$ alkyl radical or a hydroxyl group,
n is an integer ranging from 1 to 5,
m is an integer ranging from 1 to 5, and in which x is selected so that the number of amines ranges from 0.01 to 1 meq/g.

2. A composition according to claim 1, wherein said composition further comprises a cosmetically acceptable medium, wherein said washing base comprises at least one surfactant, and wherein said at least one surfactant is an anionic, amphoteric, non-ionic, zwitterionic, or cationic surfactant.

3. A composition according to claim 1, wherein said washing base is present in an amount sufficient to confer a cosmetically acceptable foaming power on the final composition.

4. A composition according to claim 1, wherein said washing base is present in an amount ranging from 4% to 50% by weight with respect to the total weight of the composition.

5. A composition according to claim 4, wherein said washing base is present in an amount ranging from 10% to 35% by weight.

6. A composition according to claim 5, wherein said washing base is present in an amount ranging from 12% to 25% by weight.

7. A composition according to claim 1, wherein said at least one cationic polymer is present in an amount ranging from 0.001% to 10% by weight with respect to the total weight of the composition.

8. A composition according to claim 7, wherein said at least one cationic polymer is present in an amount ranging from 0.005% to 5% by weight.

9. A composition according to claim 8, wherein said at least one cationic polymer is present in an amount ranging from 0.01% to 3% by weight.

10. A composition according to claim 1, wherein said at least one amine-containing silicone of formula (I) is present in an amount ranging from 0.05% to 10% by weight with respect to the total weight of the composition.

11. A composition according to claim 10, wherein said at least one amine-containing silicone of formula (I) is present in an amount ranging from 0.1% to 5% by weight.

12. A composition according to claim 11, wherein said at least one amine-containing silicone of formula (I) present in an amount ranging from 0.2% to 3% by weight.

13. A composition according to claim 1, wherein said at least one cationic polymer is a quaternary cellulose ether derivative, a cyclopolymer, or a cationic polysaccharide.

14. A composition according to claim 13, wherein said cyclopolymer is a copolymer of dimethyidiallylammonium chloride and of acrylamide.

15. A composition according to claim 13, wherein said quaternary cellulose ether derivative is formed by the reaction of hydroxyethylcellulose with an epoxide and is substituted with a trimethylammonium group.

16. A composition according to claim 13, wherein said cationic polysaccharide is a guar gum modified by a 2,3-epoxypropyltrimethylammonium salt.

17. A composition according to claim 1, wherein in the silicone of formula (I) at least one of the following is true:

$R_1$, $R_2$, $R_3$ and $R_4$ denote methyl, $R_5$ denotes methyl, n is equal to 3, or m is equal to 2.

18. A composition according to claim 17, wherein in the silicone of formula (I):

$R_1$, $R_2$, $R_3$ and $R_4$ denote methyl, $R_5$ denotes methyl, n is equal to 3, and m is equal to 2.

19. A composition according to claim 1, wherein said composition has a pH ranging from 3 to 10.

20. A composition according to claim 19, wherein said composition has a pH ranging from 5 to 8.

21. A method for cleaning and/or conditioning hair, said method comprising applying to said hair an effective amount of the detergent and conditioning composition according to claim 1 to clean and/or condition said hair.

22. The method according to claim 21, wherein said method further comprises wetting said hair before the application of said detergent and conditioning composition.

23. The method according to claim 22, wherein said method further comprises rinsing said hair following the application of said detergent and conditioning composition.

24. The method according to claim 23, wherein said method further comprises allowing said composition to remain on said wetted hair after said application and before said rinsing.

25. The composition according to claim 1, which composition is in the form of a thickened liquid, a cream, a gel, or a rinse-out lotion.

* * * * *